United States Patent [19]
Eddy

[11] Patent Number: 5,592,946
[45] Date of Patent: Jan. 14, 1997

[54] STETHOSCOPE COVER

[76] Inventor: Colleen D. Eddy, 303 Linden St., Manchester, Mass. 03104

[21] Appl. No.: 414,309

[22] Filed: Mar. 31, 1995

[51] Int. Cl.$^6$ ...................................................... A61B 7/02
[52] U.S. Cl. ........................ 128/715; 206/363; 181/131; 150/154; 383/907; 383/902
[58] Field of Search .......................... 128/715, DIG. 24; 181/131; 206/363; 383/902, 907; 150/154, 161

[56] References Cited

U.S. PATENT DOCUMENTS

| | | |
|---|---|---|
| 989,714 | 4/1911 | Lepre . |
| 1,479,614 | 1/1924 | Korhummel .......................... 383/907 |
| 3,213,960 | 10/1965 | Wagner . |
| 3,794,091 | 2/1974 | Ersek et al. . |
| 4,867,265 | 9/1989 | Wright . |
| 4,871,046 | 10/1989 | Turner . |
| 5,014,846 | 5/1991 | Walker et al. . |
| 5,022,572 | 6/1991 | Brown . |
| 5,154,164 | 10/1992 | Chikama . |
| 5,226,535 | 7/1993 | Rosdhy et al. ........................ 206/363 |
| 5,251,506 | 10/1993 | Itagaki . |
| 5,269,314 | 12/1993 | Kendall et al. . |
| 5,466,898 | 11/1995 | Gilbert et al. ........................ 181/131 |
| 5,486,659 | 1/1996 | Rosenbush ............................ 181/131 |

*Primary Examiner*—William E. Kamm
*Assistant Examiner*—Kennedy J. Schaetzle
*Attorney, Agent, or Firm*—Richard C. Litman

[57] ABSTRACT

A decorative, hypoallergenic fabric stethoscope cover is shaped like a stethoscope. The cover covers a central portion of the stethoscope and a conduit leading from the central portion of the stethoscope to a sound-input portion of the stethoscope. The cover has hook-and-loop or alternately snap fasteners for releasably closing the cover, in order to affix the cover to the stethoscope. The cover is useful for preventing allergic reactions, for increasing a stethoscope user's comfort, and for decorating a stethoscope.

8 Claims, 3 Drawing Sheets

STETHOSCOPE COVER

BACKGROUND OF THE INVENTION

1. Field of the Invention

The present invention relates generally to covers for medical devices, and more particularly to covers for stethoscopes.

2. Description of the Prior Art

A stethoscope is an essential tool for most health professionals. So important is the stethoscope to health professionals that it is standard practice for health professionals to wear a stethoscope around the neck throughout the work day. However, fair proportion of society's many health professionals would prefer not to be burdened by some of the drawbacks to wearing this essential health tool. Experience has shown that there are serious, practical problems that wearing a stethoscope can cause, problems that can interfere with a health professional's work duties. For example, stethoscopes as a rule have latex tubing that transmits sound from a sound-input or "bell" portion of a stethoscope to a listening portion of a stethoscope. This latex tubing frequently causes an allergic reaction in health professionals who wear a stethoscope around the neck. Estimates indicate that as many as 17% of all health professionals who wear stethoscopes are affected by an allergic reaction to latex in stethoscopes to a degree that is not only painful, but also disruptive of work duties. Additionally, health professionals often find that patients, especially young ones, are intimidated by healthcare processes. For a health professional to have a strange medical device wrapped around the neck only adds to this intimidation, and makes patients more difficult to work with. For these reasons, there is a substantial need for a cover for stethoscopes that is hypoallergenic, comfortable against the skin, and aesthetically appealing. The cover should be machine washable to ensure ease of re-use, thereby avoiding waste. Although many covers have been devised, no cover provides the advantages of the present invention, and no cover adequately meets the problems faced by the many health professionals who wear stethoscopes out of necessity.

U.S. Pat. No. 989,714, issued on Apr. 18, 1911, to Arcangelo Lepre, describes a watchmaker's appliance. This patent does not show a stethoscope cover.

U.S. Pat. No. 3,213,960, issued on Oct. 26, 1965, to Glen Wagner, describes a protective and insulating cover for a stethoscope's sound-input portion. This patent does not show the use of releasable fasteners nor the application of a cover to a central portion of a stethoscope, and therefore would have little value as a decorative device and no use for preventing allergic reactions in a wearer of a stethoscope.

U.S. Pat. No. 3,794,091, issued on Feb. 26, 1974, to Robert A. Ersek et al., describes a sheath for a surgical light. The sheath is meant to ensure sterility during use of the light. This patent does not show the use of releasable fasteners nor the application of a cover to a central, tubular portion of a stethoscope, and therefore would have little value as a decorative device and no use for preventing allergic reactions in a wearer of a stethoscope.

U.S. Pat. No. 4,867,265, issued on Sep. 19, 1989, to L. Bradley Wright, describes a protective and insulating cover for a stethoscope's sound-input portion. This patent does not show the use of releasable fasteners nor the application of a cover to a central portion of a stethoscope, and therefore would have little value as a decorative device and no use for preventing allergic reactions in a stethoscope user.

U.S. Pat. No. 4,871,046, issued on Oct. 3, 1989, to Kenneth R. Turner, describes a sheath for a sound-input portion of a stethoscope. The sheath is meant to ensure sterility during use of the stethoscope. This patent does not show the use of releasable fasteners nor the application of a cover to a central portion of a stethoscope, and therefore would have little value as a decorative device and no use for preventing allergic reactions in a stethoscope user.

U.S. Pat. No. 5,014,846, issued on May 14, 1991, to Scott A. Walker et al., describes a zippable protective cover for eye glasses that is integral with a strap for eye-glasses. This patent does not suggest use of a cover with a stethoscope.

U.S. Pat. No. 5,022,572, issued on Jun. 11, 1991, to Steven W. Brown, describes a zippable cover for a bicycle pump. This patent does not suggest use of a cover with a stethoscope.

U.S. Pat. No. 5,154,164, issued on Oct. 13, 1992, to Toshio Chikama, describes an anchor for an endoscope. This patent shows use of a transparent bag to cover the endoscope. This patent does not show the use of releasable fasteners nor the application of an opaque cover to a central portion of a stethoscope, and therefore would have little value as a decorative device and no use for preventing allergic reactions in a stethoscope user.

U.S. Pat. No. 5,251,506, issued on Oct. 12, 1993, to Toshio Itagaki, describes a cover for a steering wheel. This patent does not suggest use of a hypo-allergenic, decorative cover with a stethoscope.

U.S. Pat. No. 5,269,314, issued on Dec. 14, 1993, to Dwain Kendall et al., describes a thermally insulating cover for a face of a sound-input portion of a stethoscope. This patent does not show the use of releasable fasteners nor the application of a cover to a central portion of a stethoscope, and therefore would have little value as a decorative device and no use for preventing allergic reactions in a stethoscope user.

None of the above inventions and patents, taken either singly or in combination, is seen to describe the instant invention as claimed.

SUMMARY OF THE INVENTION

A decorative, hypoallergenic fabric stethoscope cover is dimensioned and configured like a central portion of a stethoscope. The cover has hook-and-loop or snap fasteners for releasably attaching a closure portion of the cover, in order to affix the cover to a stethoscope. The cover is useful for preventing allergic reactions in persons who must out of professional necessity wear a stethoscope on a regular basis. In order to prevent a free end of the stethoscope from dangling, health professionals usually wrap a tubular portion of the stethoscope partially around the neck when not using the stethoscope. In standard stethoscopes, the tubular portion that is wrapped around the neck is comprised by latex, which commonly causes painful allergic reactions that seriously detract from health professionals' comfort and work performance. Covering the tubular portion with a hypo-allergenic material prevents allergic reactions to the tubular portion.

The cover is also useful for decorating a stethoscope. Decorations on a stethoscope can have immense value to a health professional, not merely for adding interest to otherwise bland uniforms, but more importantly for distracting anxious patients from medical procedures, such as the drawing of blood. By attracting a patient's attention to an amusing stethoscope cover, a nurse for example will find it much easier to obtain the patient's cooperation during the drawing of blood or other medical procedure. The result is especially important when the patient is a young child. Having such a decoration on a stethoscope is much preferable to having it separate from a stethoscope, for the reasons that a stethoscope cover hides the intimidating stethoscope. Having such a decoration on a stethoscope is also preferable to having it separate from a stethoscope because a stethoscope—and hence the amusement value of a decorative stethoscope cover—is always right at hand, and need not be searched for.

Accordingly, it is a principal object of the invention to provide a hypoallergenic cover dimensioned and configured to cover a central portion of a stethoscope.

It is another object of the invention to provide releasable decoration for a stethoscope.

It is a further object of the invention to provide a cover for stethoscopes that is interchangeable among stethoscopes.

It is a still further object of the invention to provide a cover for stethoscopes that is machine washable and re-usable.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
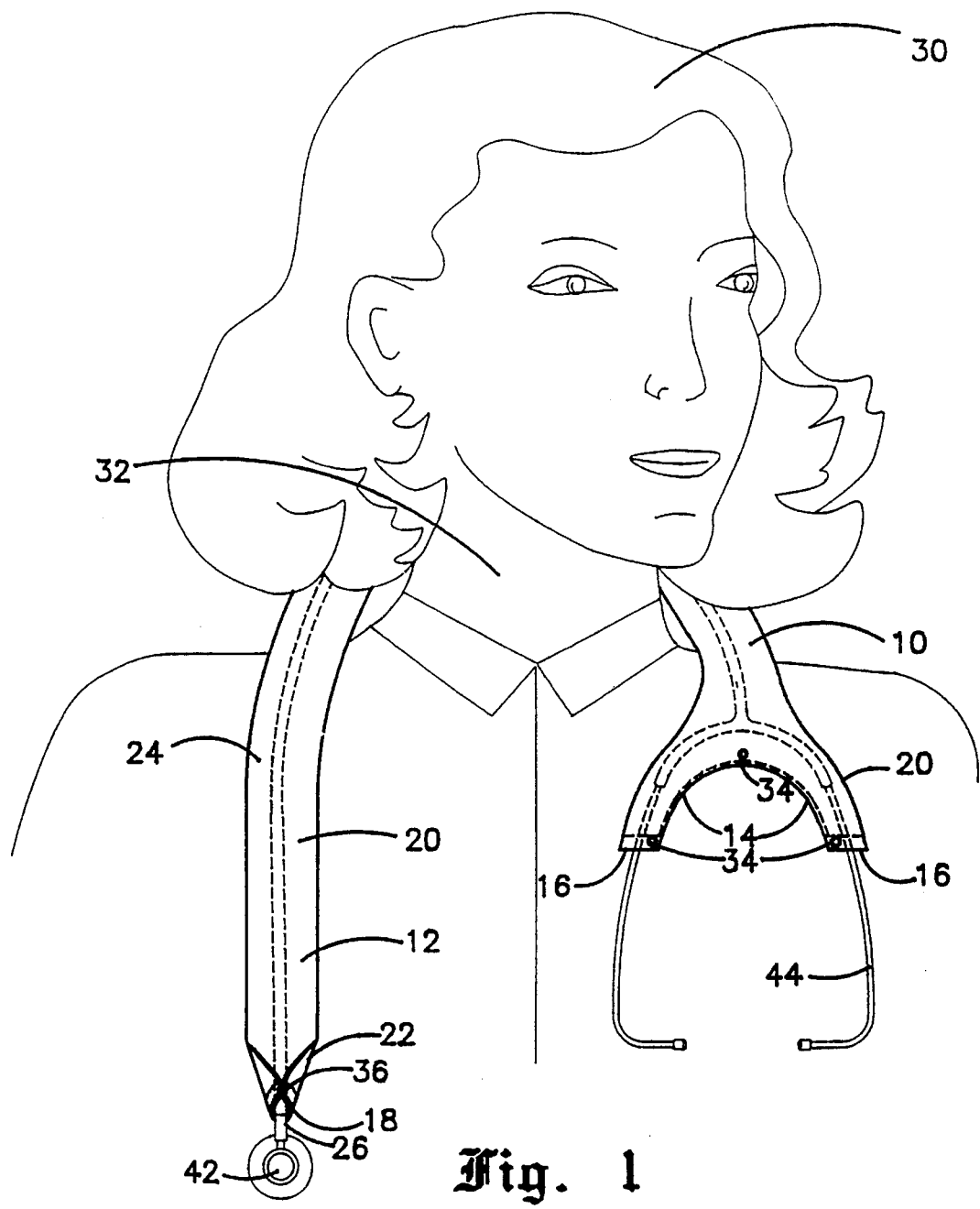
FIG. 1 is an environmental, perspective view of the stethoscope cover according to the present invention, shown partially covering a stethoscope.
Figure 2:
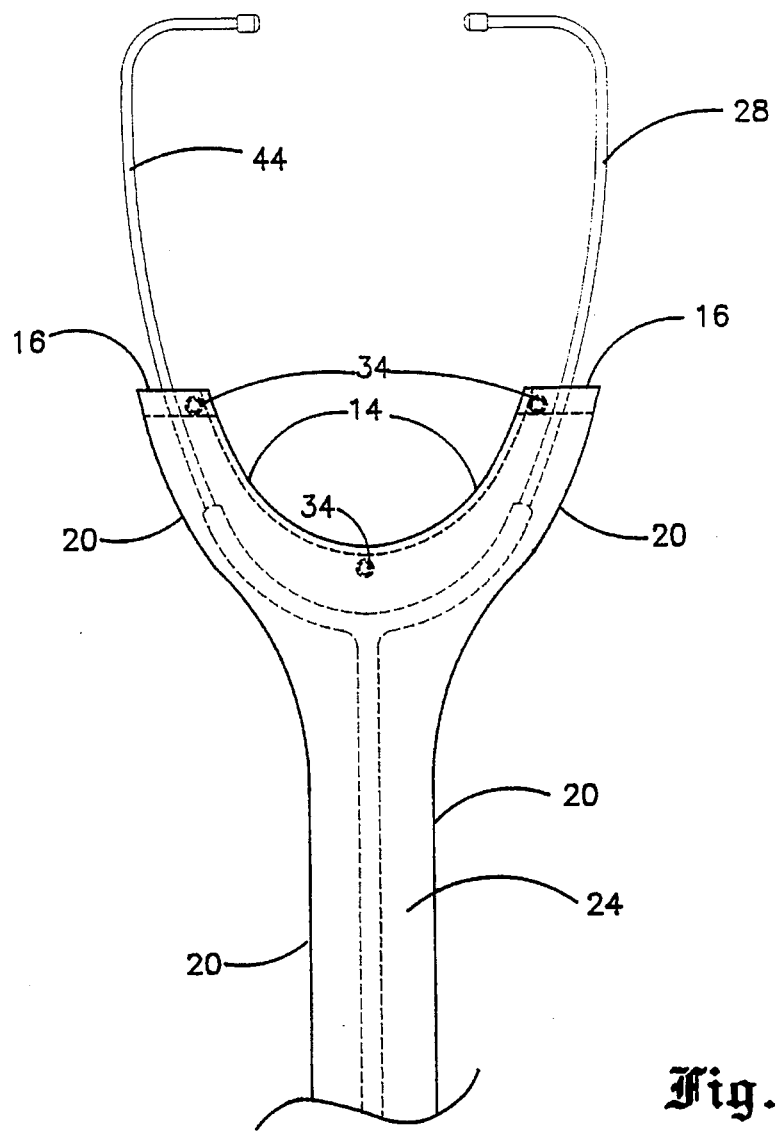
FIG. 2 is an environmental view of the stethoscope cover according to the present invention, in a closed configuration, shown with snap fasteners. Covered portions of a stethoscope are shown in dotted lines.
Figure 3:
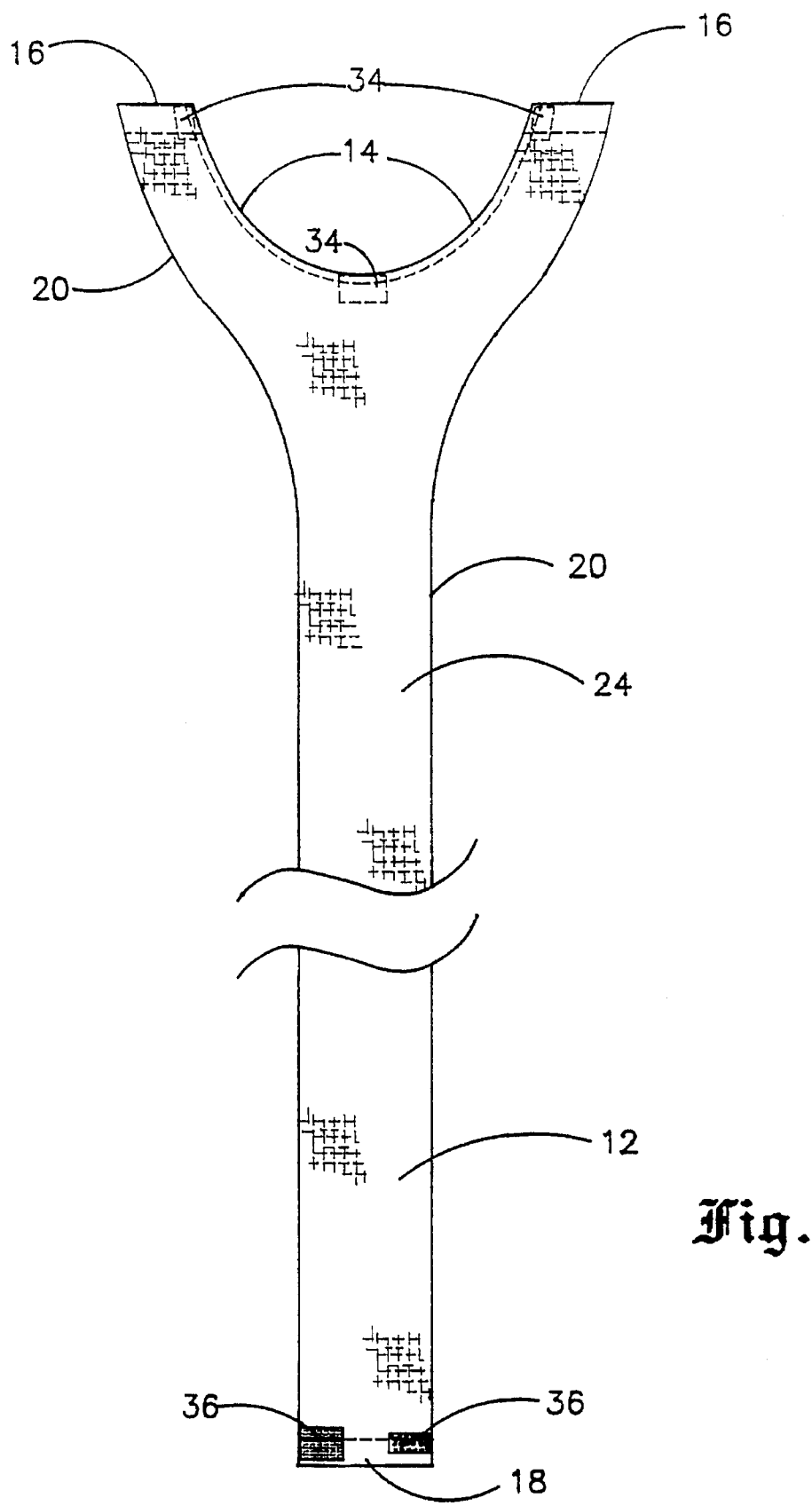
FIG. 3 is a bottom plan view of the stethoscope cover according to the present invention, in an open configuration, shown with hook-and-loop fasteners.

The present invention addresses a common problem encountered by health professionals: allergic reaction to the latex tubing of stethoscopes. It also solves the problem of an unsightly, patient-intimidating stethoscope hanging around the neck. The present invention addresses this problem by providing a hypoallergenic, comfortable cover that can be made to be aesthetically pleasing.

Referring to the drawings, the stethoscope cover 10 according to the present invention comprises a Y-shaped top panel member 12, having upper inside edges 14, top edges 16, a bottom edge 18, and outside edges 20. There is also a Y-shaped bottom panel member 22, having upper inside edges 14, top edges 16, a bottom edge 18, and outside edges 20. Both top panel member 12 and bottom panel member 22 are made out of hypoallergenic fabric 24, such as cotton, that is substantially flat and flexible, and are joined to one another at the outside edges 20, as by sewing. The panels 12, 22 are of a size that substantially covers the latex tubing 26 found in a typical stethoscope 28. Because the fabric 24 used is hypoallergenic, a person 30 wearing the stethoscope 28 around the neck 32 will not have an allergic reaction to the latex tubing 26 in the stethoscope 28. Optionally, the fabric 24 can be padded, such as by conventional polyester fill material (not shown), thereby further ensuring the comfort of a wearer 30 of a stethoscope 28.

There are upper closure members 34 disposed on upper inside edges 14. These upper closure members 34 releasably attach the top panel member 12 and the bottom panel member 22 at the upper inside edges 14. There are also bottom closure members 36 that releasably close the bottom edges 18 of the panels members 12, 22 around latex tubing 26. All the closure members 34, 36 are preferably snaps 38 or hook-and-loop fasteners 40, but could be other releasable fasteners.

In use, a bell portion 42 of a stethoscope 28 is inserted between the upper inside edges 14, through the cover 10, and out of the cover 10 through an aperture 19 between the bottom edges 18. The stethoscope 28 is fully inserted until the upper inside edges 14 cover an ear-tubing portion 44 of the stethoscope 28. At that point, the closure members 34, 36 are fastened, thereby enclosing the stethoscope 28 within the cover 10. When thus covered, the stethoscope 28 can be worn against skin, as shown in FIG. 1, without causing discomfort to the wearer 30. Additionally, decorations (not shown) on the cover 10 can increase wearing enjoyment and can provide amusement and comfort to patients, especially young patients.

It is to be understood that the present invention is not limited to the sole embodiment described above, but encompasses any and all embodiments within the scope of the following claims.

I claim:

1. A cover for a stethoscope comprising:
   a Y-shaped top panel member, said top panel member having upper inside edges, outside edges, and a bottom edge, and being substantially flat and flexible;
   a Y-shaped bottom panel member, said bottom panel member having upper inside edges, outside edges, and a bottom edge, and being substantially flat and flexible;
   said top panel member and said bottom panel member being joined at said outer edges; and
   upper closure members on said upper inside edges, said upper closure members releasably attaching said top panel member and said bottom panel member at said upper inside edges.

2. The cover according to claim 1, further comprising lower closure member on said top panel member bottom edge, said lower closure member releasably attaching said top panel member bottom edge to itself to define an aperture.

3. The cover according to claim 2, wherein said closure members are snaps.

4. The cover according to claim 2, wherein said closure members are hook-and-loop fasteners.

5. The cover according to claim 1, wherein said panel members are dimensioned and configured to cover a central portion of a stethoscope.

6. The cover according to claim 5, wherein said central portion comprises latex tubing.

7. The cover according to claim 1, wherein said panel members are comprised by hypoallergenic fabric.

8. The cover according to claim 1, wherein said panel members are padded.

\* \* \* \* \*

UNITED STATES PATENT AND TRADEMARK OFFICE
CERTIFICATE OF CORRECTION

PATENT NO. : 5,592,946
DATED : JANUARY 14, 1997
INVENTOR(S) : COLLEEN D. EDDY

It is certified that error appears in the above-indentified patent and that said Letters Patent is hereby corrected as shown below:

On the title page, Item [76], change "Mass." to --N.H.--.

Signed and Sealed this

Fourteenth Day of October, 1997

Attest:

BRUCE LEHMAN

Attesting Officer

Commissioner of Patents and Trademarks